United States Patent [19]

Martin et al.

[11] Patent Number: 5,015,230

[45] Date of Patent: May 14, 1991

[54] ANGIOPLASTY CATHETER WITH SPIRAL BALLOON

[75] Inventors: Geoffrey S. Martin; Anand Ram, both of Mississauga, Canada

[73] Assignee: Vas-Cath Incorporated, Mississauga, Canada

[21] Appl. No.: 472,007

[22] Filed: Jan. 30, 1990

[30] Foreign Application Priority Data

Jan. 30, 1989 [CA] Canada ................................. 589510

[51] Int. Cl.⁵ .............................................. A61M 29/00
[52] U.S. Cl. ..................................... 604/96; 604/103; 604/281; 606/194
[58] Field of Search ................ 604/96, 103, 264, 280, 604/281; 606/192–196; 600/18

[56] References Cited

U.S. PATENT DOCUMENTS

| | | | |
|---|---|---|---|
| 4,261,339 | 4/1981 | Hanson et al. | 604/96 |
| 4,276,874 | 7/1981 | Wolvek et al. | 604/96 |
| 4,292,974 | 10/1981 | Fogarty et al. | 606/194 |
| 4,327,709 | 5/1982 | Hanson et al. | 604/96 |
| 4,402,307 | 9/1983 | Hanson et al. | 600/18 |
| 4,467,790 | 8/1984 | Schiff | 604/96 |
| 4,646,719 | 3/1987 | Newman et al. | 606/192 |
| 4,655,748 | 4/1987 | Mushika | 604/96 |
| 4,681,092 | 7/1987 | Cho et al. | 604/96 |
| 4,848,342 | 7/1989 | Kaltenbach | 606/194 |
| 4,897,077 | 1/1990 | Cicciu et al. | 606/195 |

FOREIGN PATENT DOCUMENTS 256683  2/1988  European Pat. Off. ............ 604/96

*Primary Examiner*—Stephen C. Pellegrino
*Assistant Examiner*—Ralph A. Lewis
*Attorney, Agent, or Firm*—Rogers & Scott

[57] ABSTRACT

The invention provides a balloon of non-elastomeric material which is spirally wrapped onto the main body of the catheter. The catheter is inserted in this condition and on inflation, the balloon aligns itself with the axis of the main body causing the body within the balloon to twist and store energy which is available for collapsing the balloon after use.

8 Claims, 3 Drawing Sheets

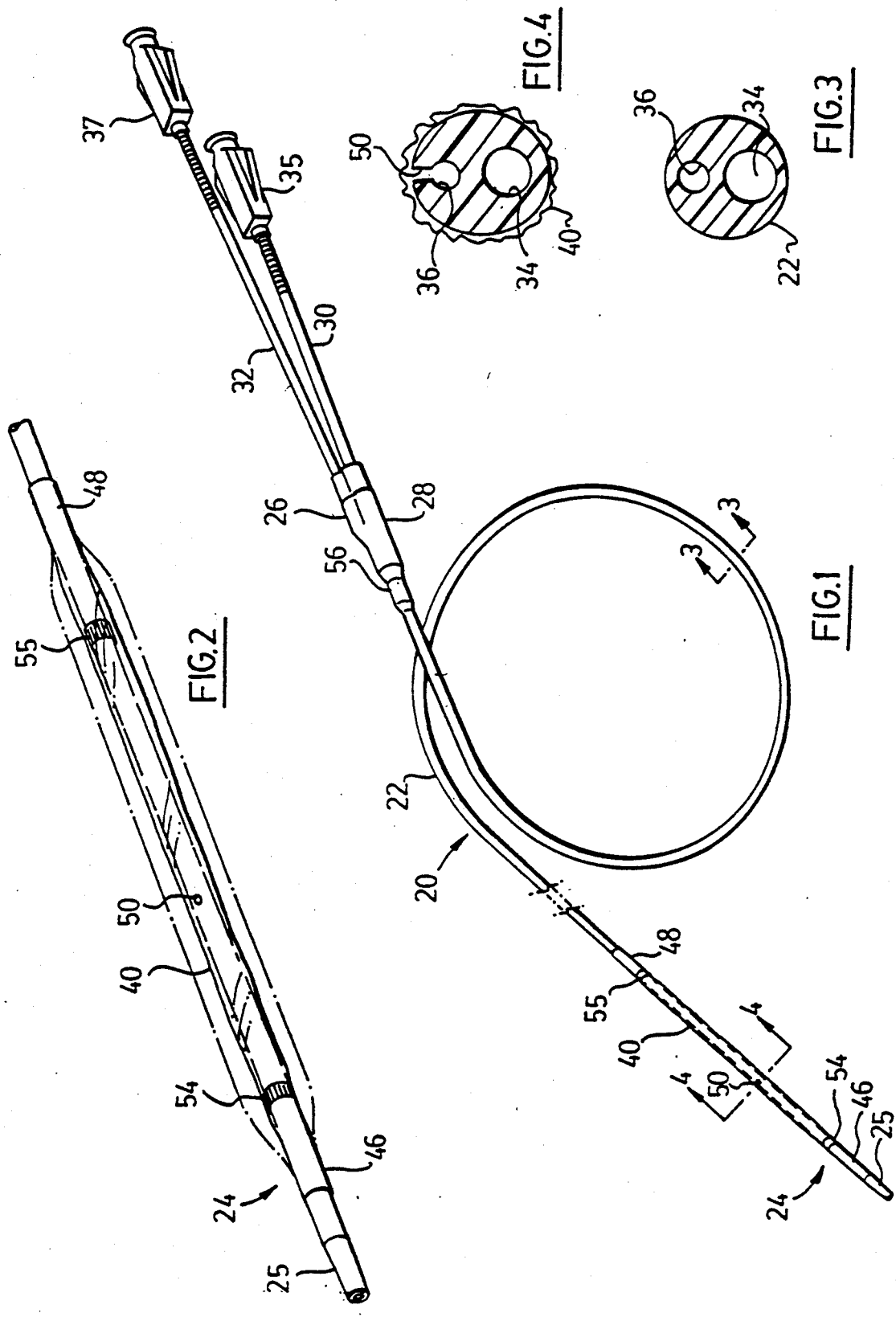

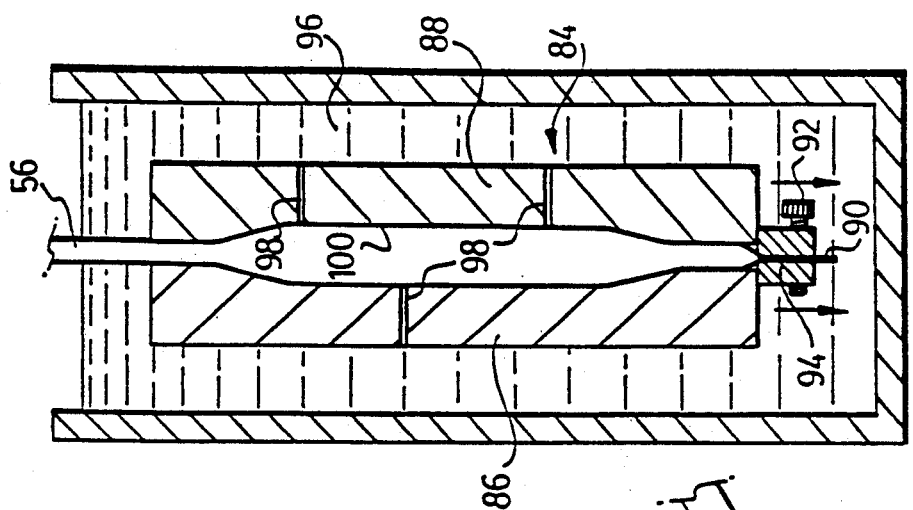
FIG.7
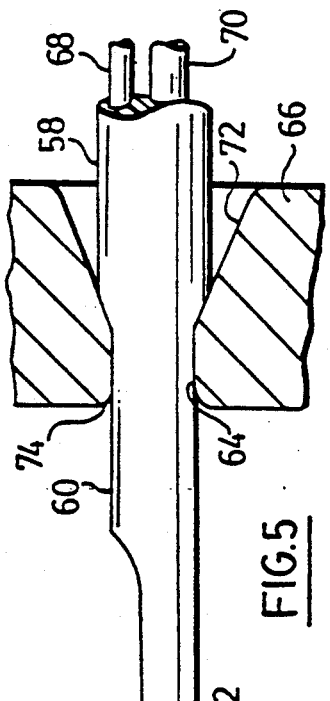
FIG.5
FIG.6
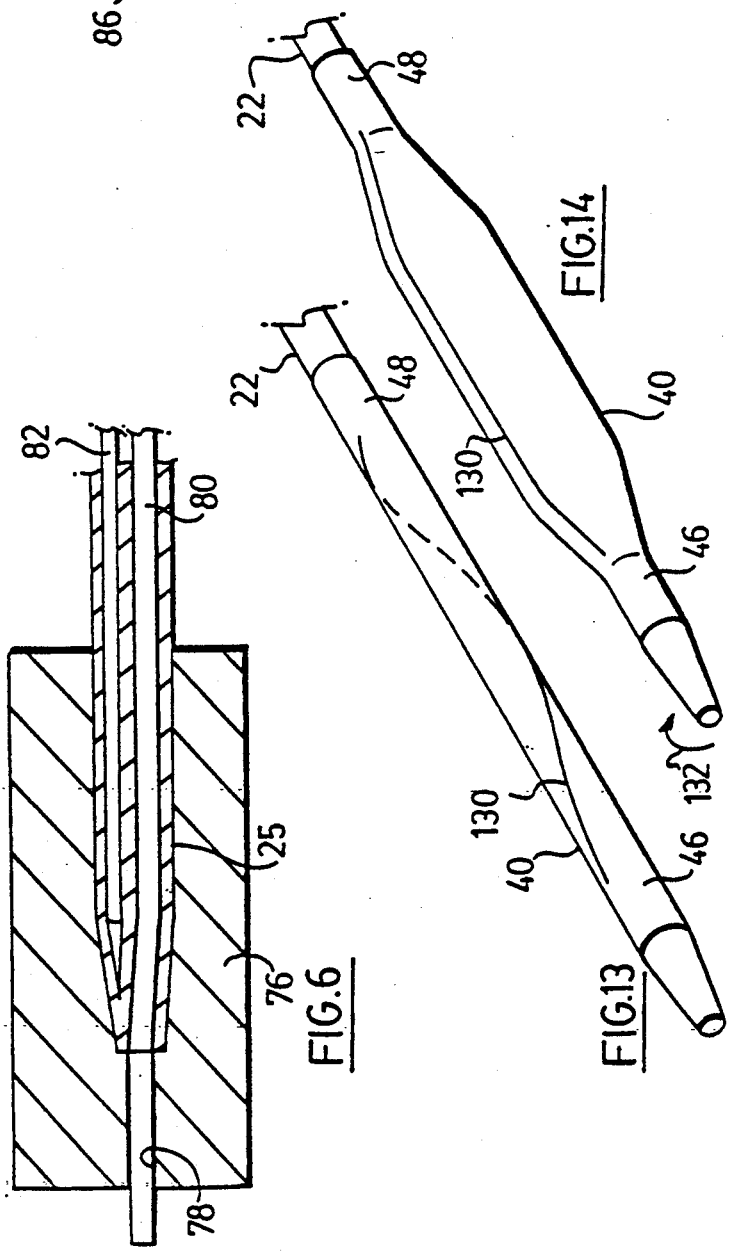
FIG.14
FIG.13

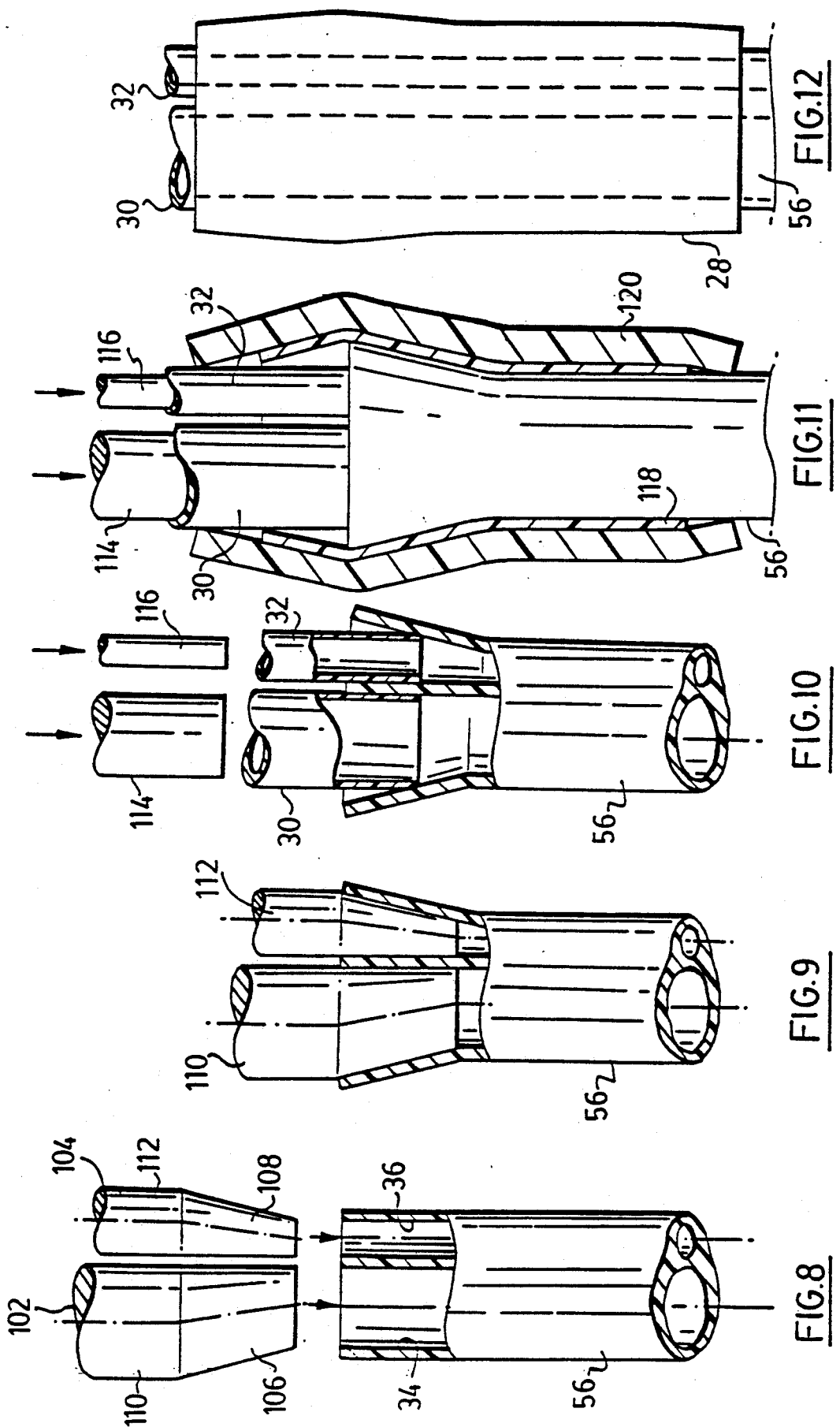

ANGIOPLASTY CATHETER WITH SPIRAL BALLOON

This invention relates to angioplasty catheters for use in the treatment of stenosed blood vessels. The invention also relates to a method of manufacturing the catheter.

BACKGROUND OF THE INVENTION

An angioplasty catheter is typically elongate and tubular, and is provided with a balloon near or at its distal end and radiopaque bands defining the extremities of the balloon. The catheter is inserted at a convenient location and fed into the stenosed blood vessel until the balloon is located in the narrowed portion of the blood vessel. Fluid from an external supply is then used to inflate the balloon such that it compresses the obstructing plaque and stretches the plaque coated walls of the blood vessel. When the physician is satisfied that the blood vessel has been widened sufficiently, the balloon is deflated and the catheter removed.

Angioplasty catheters have been successfully used for a number of years in the treatment of blood vessels obstructed or stenosed with plaque. An angioplasty catheter includes, near its distal end, a balloon which can be inflated by means of pressurized fluid supplied through a lumen in the catheter. The treatment involves the location of the balloon in the stenosed section of the blood vessel, followed by inflation and deflation. During inflation, the balloon compresses the plaque and stretches the blood vessel such that the cross-sectional area of the stenosis is increased until it is comparable to that of the unobstructed blood vessel. When the treatment has been completed the balloon is deflated and the catheter removed. The treated blood vessel maintains substantially its enlarged cross-section to permit the free flow of blood through this portion.

To perform satisfactorily a suitable angioplasty catheter must possess a number of properties. For ease of insertion it is preferable that the catheter is flexible, has a relatively small cross-sectional area, and has a smooth outer surface. Also, the method of insertion of the catheter has a significant bearing on the form of the catheter. The catheter which is the subject of the present invention is intended for insertion using the Seldinger technique and therefore preferably has a tapered end and a lumen to receive the Seldinger guide wire. The catheter ends at an aperture in the tapered end substantially coaxially with the main body of the catheter. However, perhaps the most important part of the catheter is the balloon which must be strong enough to withstand the application of high pressures without rupture and which must always inflate to a predetermined shape and size.

Also, during insertion and removal, the balloon must present a small profile as it is moved longitudinally.

It has long been accepted that in order to reduce the balloon profile during insertion, the balloon must be wrapped in some way about the body. An example of a typical structure intended for this purpose is found in U.S. Pat. No. 4,338,942 to Fogarty. The balloon is attached to an internal rod which has an exposed control knob at the proximal end of the catheter. On turning the knob, the balloon is rotated at the distal end to impart a twist which wraps the balloon on the main body. There is no energy stored other than possibly in the balloon. After insertion, the twist is removed to allow inflation and then, to permit removal, the twist is again applied. This structure is rather complex and requires a long rod through the length of the device. Further, this structure is not suitable for insertion using the Seldinger technique.

Another exemplary structure which uses a mechanical wrapping device is shown in U.S. Pat. No. 4,646,719 to Neuman et al. A tube runs the length of the device to permit Seldinger insertion through the tube and this tube can be rotated to wrap the balloon against the resistance of a spring. After insertion, the spring energy can return the balloon to its normal position for inflation. During insertion the balloon must be kept in the wrapped condition against the urging of the spring which will tend to unwrap the balloon.

A different approach is taught in U.S. Pat. No. 4,402,307 to Hanson et al. A balloon is provided which is attached at its distal end to a tubular central member which extends along the length of the catheter. A tool is provided for engaging the distal end to rotate that end and wrap the balloon around the tube as energy is stored in the twisted tube. Provided that sufficient vacuum is applied, the balloon will remain in this condition during insertion. Should there be any difficulty with the vacuum then of course the balloon will unwrap itself under the influence of the tube returning to its normal condition. After insertion, the balloon is released and can not be wrapped again in the same fashion in which it was wrapped in the first place. However access is provided to the tube at the proximal end for rotating the tube which will presumably wrap the balloon in the fashion taught by Fogarty.

All of the prior art structures suffer from serious disadvantages and among them are complexity, dangerous situations arising should vacuum fail during insertion, and such difficulties as unwrapping the balloon accurately to ensure that it is in the proper position for inflation after it is located in the patient.

It is an object of the present invention to provide an improved angioplasty catheter which overcomes some of the disadvantages of the prior art.

SUMMARY OF THE INVENTION

The invention provides a balloon of non-elastomeric material which is spirally wrapped onto the main body of the catheter. The catheter is inserted in this condition and on inflation, the balloon aligns itself with the axis of the main body causing the body within the balloon to twist and store energy which is available for collapsing the balloon after use.

BRIEF DESCRIPTION OF THE DRAWINGS

FIG. 1 is a perspective view of an angioplasty catheter in accordance with a preferred embodiment of the present invention;

FIG. 2 is an enlarged isometric view of a balloon forming part of the catheter;

FIG. 3 is a sectional view on line 3—3 of FIG. 1;

FIG. 4 is a sectional view on line 4—4 of FIG. 1;

FIG. 5 is a diagrammatic sectional view illustrating the drawing of the main body to reduce cross-section and to change the physical characteristics of the main body of the catheter;

FIG. 6 is a sectional view illustrating the method of manufacturing a tip on the catheter;

FIG. 7 is a diagrammatic sectional view illustrating a method of manufacturing the balloon;

FIGS. 8 to 12 are views, mostly in section, illustrating the method of manufacturing the junction at the proximal end where tubes provide access for a Seldinger wire and for providing a supply of fluid to inflate the balloon; and FIGS. 13 and 14 are diagrammatic views illustrating the operation of the balloon as it moves from a collapsed to an inflated condition.

DESCRIPTION OF THE PREFERRED EMBODIMENT

The preferred embodiment of the angioplasty catheter according to the present invention will now be described in detail, firstly with reference to FIG. 1 of the drawings. This view shows in perspective an angioplasty catheter, designated generally by the numeral 20, including a flexible main body 22 having a distal end or tip 24 defining a tapered tip 25 to facilitate insertion into a vein of a patient, and a proximal end 26 for connection, by means of connection piece 28, to the respective distal ends of a guide wire tube 30 and a fluid supply tube 32. The tubes 30, 32 are in communication with respective circular guide wire and fluid supply lumens 34, 36 defined within the main body 22 (FIG. 3) and are provided with luer fittings 35, 37 at the respective proximal ends. Different colored marking sleeves 38, 39 help distinguish the tubes from one another (although in practice the fluid supply lumen 36 is of significantly smaller cross-section than lumen 34).

The body 22 extends from the connection piece 28 to the tip 24 and passes through a balloon 40, details of which are provided below. A tubular shipping protector (not shown) for location over the distal end 24 and balloon 40 would normally be provided to protect the balloon and to retain it in a collapsed condition ready for insertion.

Reference is now made to FIG. 2 of the drawings which shows the distal end of the catheter in greater detail with the balloon in a collapsed condition. The balloon 40, located at the distal end 24, is formed of a Nylon membrane which is flexible and substantially inextensible (i.e. not elastomeric) and, when inflated, is in the form of a cylinder having tapering ends (as indicated in ghost outline). The distal and proximal ends 46, 48 of the membrane locate snugly over the distal end 24 of the main body 22 with the distal end 46 being mated to the body just short of the tapered tip 25. A side opening or aperture 50 in the wall of the main body 22 provides fluid communication between the smaller fluid supply lumen 36 and the interior of the balloon 40 between the body 22 and the membrane of the balloon.

A pair of radiopaque bands 54, 55 are attached around the body 22 inside the balloon 40 and near the ends 46, 48 for monitoring the position of the balloon.

To inflate the balloon 40, fluid is supplied under pressure through the fluid supply tube 32 and the fluid supply lumen 36, and then through the aperture 50 into the balloon 40. Thus, the balloon is pushed radially outwardly by the fluid pressure to assume the shape shown by the chain-dotted lines in FIG. 2, so that the balloon 40 has a diameter greater than that of the main body 22. On deflation, and on withdrawing the fluid by suction (i.e. negative pressure) the balloon folds and collapses to lie close to the outer surface of the body, as shown in FIGS. 2 and 4.

Reference is next made to FIG. 5 which illustrates diagrammatically how the main body 22 is drawn down. As seen in FIG. 1, the main body meets, adjacent the connection piece 28, a short portion 56 of larger diameter than the main body 22. This corresponds to the diameter at portion 58 in FIG. 5 and a diameter 60 corresponds to that of the main body. The purpose of this reduction in diameter will be explained in more detail later but for the moment it is sufficient to understand how it is accomplished. A length of extruded Nylon having a cross-section similar to that shown in FIG. 3, but of the diameter of portion 58, is first cut to remove some material to leave a leading end piece 62. This piece is small enough to pass readily through an opening 64 in a heated die 66. A pair of supporting rods 68, 70 are engaged in the respective lumens 34, 36 (FIG. 3) and have proportions corresponding to the required sizes of these lumens as drawn in FIG. 3. Of course the rods will be loose in the original extrusion because it is of larger size than the body 22.

The die 66 includes a conical lead-in portion 72 which blends smoothly into the polished opening 64, and at the outlet, a rounded nose portion 74 is provided so that after extrusion, the body can be drawn backwards through the die to remove it.

After cutting the extrusion to provide the end piece 62, the rods 68, 70 are engaged and the end piece 62 fed through the heated die to be used to draw the remaining extrusion through the die. This drawing process takes place to effectively orientate molecular structure, improve the surface finish, and enhance the density of the Nylon to give it better torsional stiffness and strength. This continues in the manner illustrated in FIG. 5 until the portion 56 (FIG. 1) is reached, at which point the drawing is discontinued and the body is withdrawn in the opposite direction from the die 66. An end part, including the leading end piece 62, is cut off the extrusion leaving only the required part of the body. The length of the catheter can be fixed at this stage.

The next step in the process is to form the tip 25 (FIG. 1) and the method of doing this is illustrated diagrammatically in FIG. 6. Here a heated die 76 has an internal shape corresponding to that of the required tip and an opening 78 aligned with the tip to receive an end part of the mandrel 80 which is engaged through the guide wire tube of the body. A rod or mandrel 82 is provided in the fluid supply tube and, under the influence of heat from the die 76, the body is advanced into the die and deformed into the shape shown in FIG. 6. It will be seen in this FIG. that the fluid supply tube has been terminated at its end whereas the guide wire tube has been retained in an open condition to provide access for the Seldinger wire during insertion. The form of the structure is such that the end is conical so that the Seldinger wire is centered relative to the catheter during insertion.

As a separate procedure, a membrane is formed to be used to make the balloon. This procedure is illustrated diagrammatically in FIG. 7. A tube of Nylon having a wall diameter thickness of about 0.015 inches is located in a copper mould 84 made up of two halves 86, 88. The tube 56 is cut at a lower end 90 and a clamp 92 is attached to a short end piece 94 which extends from the mould 84 to seal the end of the tube and to ensure that the tube is not pulled from the mould. The tube and mould are then suspended in a heated oil bath 96 at about 170° to 175° C. for three minutes. The total weight of the mould and accessories is about 150 gm. and this weight tends to stretch the heated tube such that the molecular orientation becomes axial along the length of the tube.

After three minutes in the oil bath 96 a pressure of 400 p.s.i. is applied to the inside of the tube from an external supply (not shown) causing it deform to occupy the interior of the mould, oil in the mould being pushed from the mould through relief holes 98. After a short interval of time the pressure is released and the mould containing the resulting membrane 100 is removed from the oil bath and placed in freon which acts as a coolant and disperses the oil. The membrane retains the tapered cylindrical shape of the mould, the deformed portion having a wall thickness in the order of 0.00025 to 0.0005 inches.

Reference is next made to FIG. 8 which is the first of a series of FIGS. 8 to 12 demonstrating the manufacture of the connection piece 28 shown in FIG. 1. The portion 56 of the main body is held in place to receive, under the influence of some heat, a pair of mandrels 102, 104. These mandrels have leading ends corresponding to the sizes of the respective guide wire tube 30 and fluid supply tube 32, and leading end portions 106, 108 are conical with the axis inclined as indicated by the chain dotted center lines to meet cylindrical portions 110, 112 of the mandrels. This arrangement is necessary since they are to be used to form an end of the main body and deformation can only take place outwardly. The mandrels are entered into the lumens 34, 36 to the position shown generally in FIG. 9 where it will be seen that the ends of the lumens have been flared. Next, and as seen in FIG. 10 diagrammatically, the distal ends of the respective guide wire tube 30 and fluid supply tube 32 are engaged in the flared ends of the lumens 34, 36 followed by a pair of suitably proportioned mandrels 114, 116 which are engaged through the tubes and into the body portion 56. The tubes and body are of Nylon which is a thermoplastic material so that deformation of these parts can be achieved to bring them together in a single assembly.

As seen in FIG. 11, a thin sleeve 118, of a Nylon material is engaged over the body portion 56 and extending outwardly beyond this portion terminating around the tubes 30, 32. Over this is applied a heavy sleeve 120 of silicon rubber which is stretched into place. The assembly is then heated and compressed in a suitable clamping arrangement such as a pair of formed die halves (not shown) to bring the materials into flowing engagement with the mandrels and to seal the Nylon parts to one another. The silicon rubber sleeve 120 helps to distribute the load and to apply a circumferential compressive loading on the parts to cause flowing around the mandrels.

The resulting structure looks generally like that shown in FIG. 12. The tubes 30, 32 are supported where they meet the connection piece and the internal surfaces are smooth since they were formed around the mandrels 114, 116 which of course are withdrawn after the procedure is completed.

The procedure described with reference to FIGS. 8 to 12 can be varied by using different sleeve arrangements and even by building up several sleeves one over another to provide more material flowing and to enhance the strength of the structure.

Turning now to the balloon, after manufacture as described the reference to FIG. 7, the ends are trimmed, and it is positioned on the main body and secured in place using a suitable adhesive. If preferred, the balloon can be bonded to the main body.

FIG. 13 illustrates diagrammatically the balloon in position on the main body 22. For simplicity the wrinkles that will inevitably appear in the balloon are omitted and an imaginary line 130 is drawn on the balloon in a spiral to indicate that the balloon has been attached in this fashion. In other words, the proximal end of the balloon 48 was attached to the main body 22, the balloon twisted about the axis of the body 22 and then the distal end 46 attached so that the balloon has a spiral twist in it. As mentioned previously, there is a molecular orientation which will be along lines such as line 130. The balloon therefore will have a tendency on inflation to take up its normal shape as manufactured in the process described with reference to FIG. 7. Consequently, after inflation the balloon will take on the position shown in FIG. 14 where the line 130 has become axial. In order to accommodate this, the portion of the main body defined between the distal and proximal ends 46, 48 will be subject to a torque indicated by the arrow 132 resulting in this portion of the body receiving an axial twist thereby storing energy in the body. Upon removing the pressure from the balloon 40, the energy stored in the body will return the balloon to the FIG. 3 position (or substantially so) thereby again storing the balloons snugly about the body 22 for removal.

It is of course to be appreciated that angioplasty catheters of the type described are not reused. The energy stored in the body 22 would eventually affect the body if it were used repeatedly but this is not the case in this structure.

In the preferred embodiment the main body has an outside diameter of 5 French (about 0.065 inches) with guide wire lumen about 0.037 inches and fluid supply lumen about 0.017 inches. The portion 56 (which corresponds to the original extrusion) is 7 French (about 0.090 inches), and the lumens 0.039 and 0.024 inches in diameter. The ends of the balloon are twisted relative to one another by about 360 to 540 degrees.

This embodiment and others are within the scope of the invention as defined and claimed.

What is claimed is:

1. An angioplasty catheter comprising:
    an elongate tubular main body having proximal and distal ends and including a fluid supply lumen extending longitudinally, and a side opening in the main body adjacent the distal end, the lumen terminating at the side opening;
    a balloon of non-elastomeric material having ends spaced apart and attached at the ends of the balloon to the main body with one of the ends adjacent said distal end and the balloon containing the side opening, the balloon being twisted spirally between said ends of the balloon to store the balloon close to the main body in a collapsed condition; and
    the main body being resiliently deformable within the balloon when the balloon is inflated to thereby store torsional energy in the main body for use in returning the balloon to the collapsed condition during deflation of the balloon.

2. An angioplasty catheter as claimed in claim 1 and further comprising radiopaque bands on the main body and adjacent ends of the balloon to define the location of the balloon during insertion procedures.

3. An angioplasty catheter as claimed in claim 1 in which the main body further defines a guide wire lumen extending in parallel with the fluid supply lumen and extending between the proximal and distal ends of the catheter.

4. An angioplasty catheter as claimed in claim 3 and further comprising a connection piece at the proximal end of the main body and guide wire and fluid supply tubes coupled to said piece for communication between the guide wire and fluid supply tubes and the respective guide wire and supply lumens.

5. An angioplasty catheter as claimed in claim 4 in which the main body, and the guide wire and fluid supply lumens are of circular cross-section.

6. An angioplasty catheter as claimed in claim 5 in which the said distal end of the main body is tapered and the guide wire lumen terminates centrally of the tapered end.

7. An angioplasty catheter comprising:

an elongate tubular main body having proximal and distal ends and defining guide wire and fluid supply lumens, and a tapered tip at the distal end, the fluid supply lumen being closed at the tip and the guide wire lumen extending to the tip for receiving a wire to guide the catheter during insertion procedures, a side opening in the main body at the end of the supply lumen near the tip;

a balloon sealed to the main body near the tip and containing said side opening, the balloon being of a non-elastomeric material and having a defined shape when inflated from a collapsed condition to the inflated condition by fluid pressure applied through the supply lumen, the balloon being twisted when assembled on the main body, so that on inflation the main body will be twisted thereby storing energy for use in restoring the balloon to the collapsed condition;

a portion of larger cross-section at the proximal end of the main body and formed integrally with the main body of thermoplastic material, said portion being an extrusion and the main body being formed from the extrusion by drawing the extrusion through a heated die while supporting the lumens to give the main body a reduced cross-section, longitudinal molecular orientation, and enhanced surface smoothness;

a connection piece at the proximal end of said portion and coupled to said portion; and guide wire and fluid supply tubes coupled to the connection piece in communication with the respective guide wire and fluid supply lumens.

8. A method of making an angioplasty catheter having an elongate tubular main body including proximal and distal ends and containing a guide wire lumen and a fluid supply lumen, and a balloon attached to the main body in fluid communication with the fluid supply lumen to inflate the balloon, the method comprising selecting a main body including at least a portion adjacent the distal end having torsional flexibility, attaching an inextensible balloon to the main body to contain at least part of said portion, the balloon being twisted spirally before attachment for maintaining a collapsed condition prior to use, whereby on pressurising the by passing fluid down the fluid supply lumen, the balloon will inflate straightening as it inflates and thereby twisting said portion to store energy which is available to return the balloon to the collapsed condition.

* * * * *